United States Patent

Meadows et al.

Patent Number: 5,325,723
Date of Patent: Jul. 5, 1994

[54] CORE SAMPLE TEST METHOD AND APPARATUS

[75] Inventors: David L. Meadows, Rush Springs, Okla.; Stewart E. Rowell, White Hall, Ark.

[73] Assignee: Halliburton Company, Duncan, Okla.

[21] Appl. No.: 985,396

[22] Filed: Dec. 4, 1992

[51] Int. Cl.$^5$ ............................................. G01N 3/00
[52] U.S. Cl. ...................................... 73/794; 73/38; 73/153; 364/422; 100/106; 378/208
[58] Field of Search ......................... 73/794, 153, 38

[56] References Cited

U.S. PATENT DOCUMENTS

| | | | |
|---|---|---|---|
| 4,495,795 | 1/1985 | Gupta | 73/38 |
| 4,599,891 | 7/1986 | Brauer et al. | 73/38 |
| 4,691,558 | 9/1987 | Vinson et al. | 73/64.1 |
| 4,868,751 | 9/1989 | Dogru et al. | 364/422 |
| 4,996,872 | 3/1991 | Mueller et al. | 73/38 |
| 5,050,493 | 9/1991 | Prizio et al. | 100/106 |
| 5,065,421 | 11/1991 | Morineau et al. | 378/208 |
| 5,226,310 | 7/1993 | Steiger | 73/794 X |

FOREIGN PATENT DOCUMENTS

| | | | |
|---|---|---|---|
| 794434 | 1/1977 | U.S.S.R. | |
| 1364708 | 1/1988 | U.S.S.R. | 73/153 |
| 1716376 | 2/1992 | U.S.S.R. | 73/794 |

OTHER PUBLICATIONS

A Temco, Inc. catalog entry for a "Resistivity Core Holder, ECH Series" believed to be published prior to Sep., 1991.
A Halliburton Services design of a temperature control cell disclosed or in use prior to Sep., 1991, labeled Exhibit 1.
A Temco, Inc. catalog entry for an "Incremental Pressure Core Holder, DCH Series" believed to be published prior to Sep., 1991.
A Temco, Inc. catalog entry for a "Medium Pressure Permeability Core Holder, RCH Series" believed to be published prior to Sep., 1991.
A Temco, Inc. catalog entry for a "High Pressure Permeability Core Holder, HCH-4" believed to be published prior to Sep., 1991.
A Temco, Inc. catalog entry for a "Medium Pressure Core Holder, RCH Series" believed to be published prior to Sep., 1991.
A Temco, Inc. catalog entry for a "High Pressure Permeability Core Holder RCH Series" believed to be published prior to Sep., 1991.
A Temco, Inc. entry for "Core Holders For Permeability Testing, MCH-I Series" believed to be published prior to Sep., 1991.

Primary Examiner—Hezron E. Williams
Assistant Examiner—James M. Olsen
Attorney, Agent, or Firm—Robert A. Kent; E. Harry Gilbert, III

[57] ABSTRACT

A core sample from an oil or gas well can be quickly and easily inserted and removed relative to a reusable sealing sleeve fixed within a test housing wherein the core sample is tested for both longitudinal and lateral strain in response to applied stress. Young's modulus and Poisson's ratio can be determined from the strain and stress information. Pressures and temperature can be set to simulate downhole conditions inside the apparatus.

6 Claims, 3 Drawing Sheets

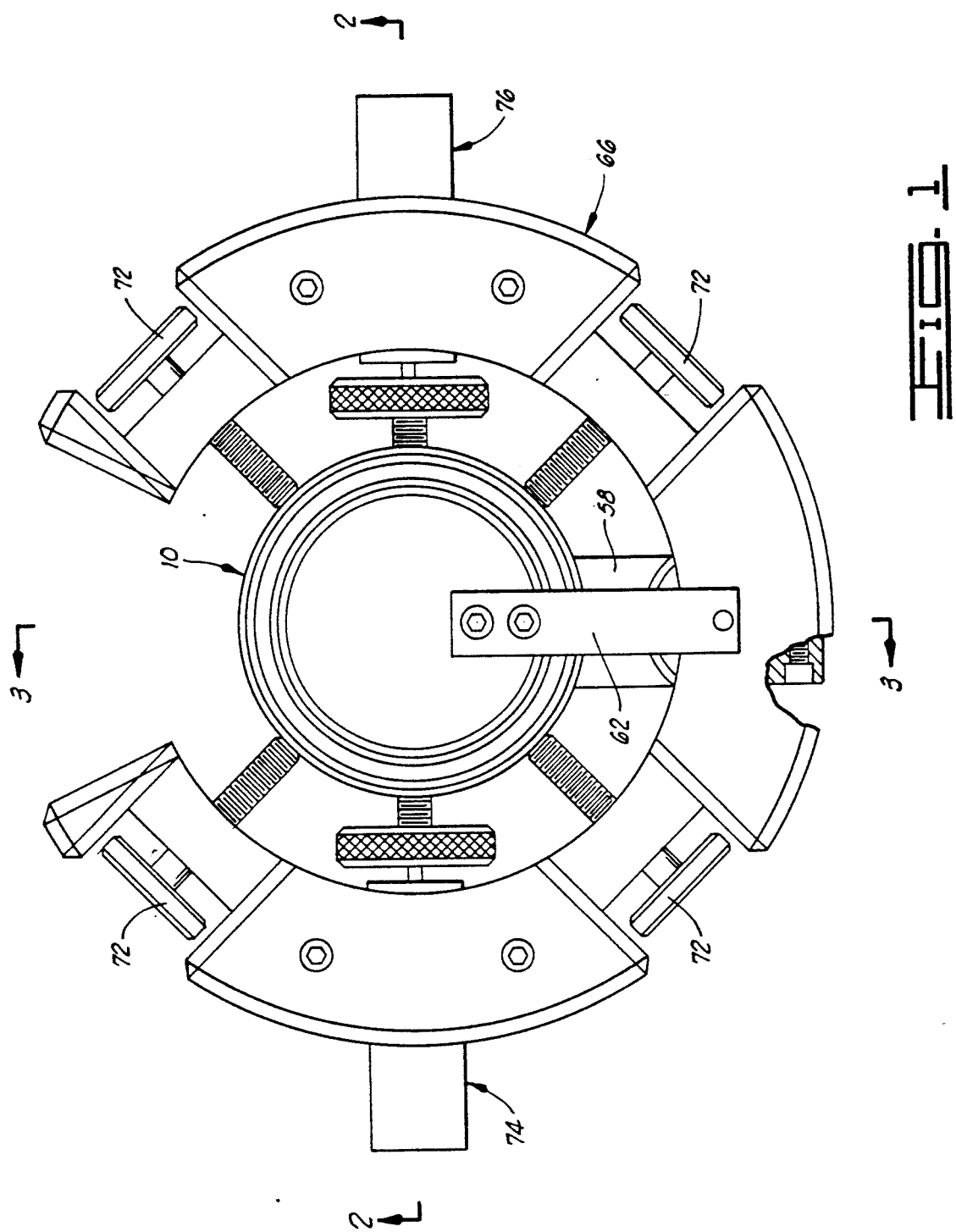

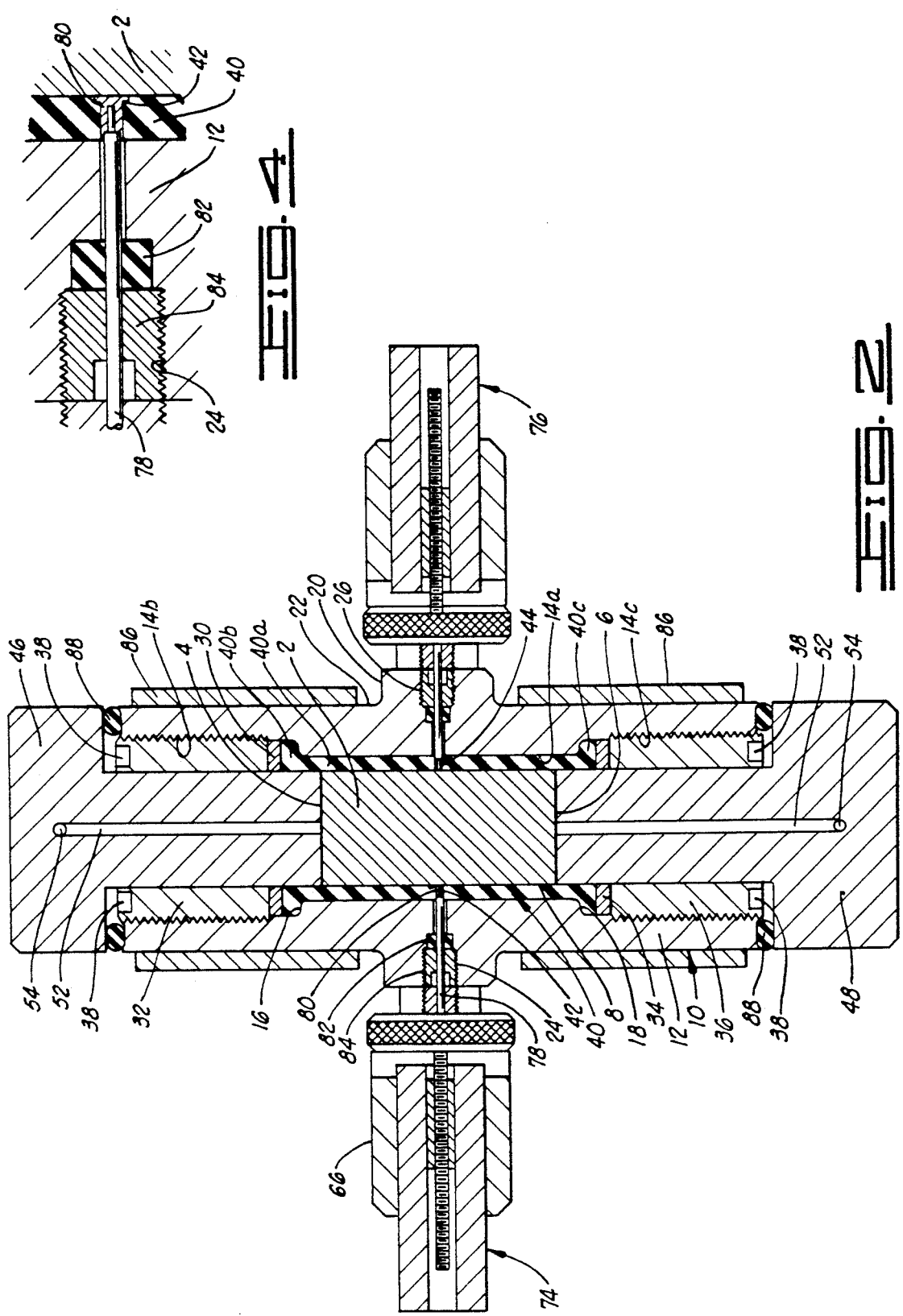

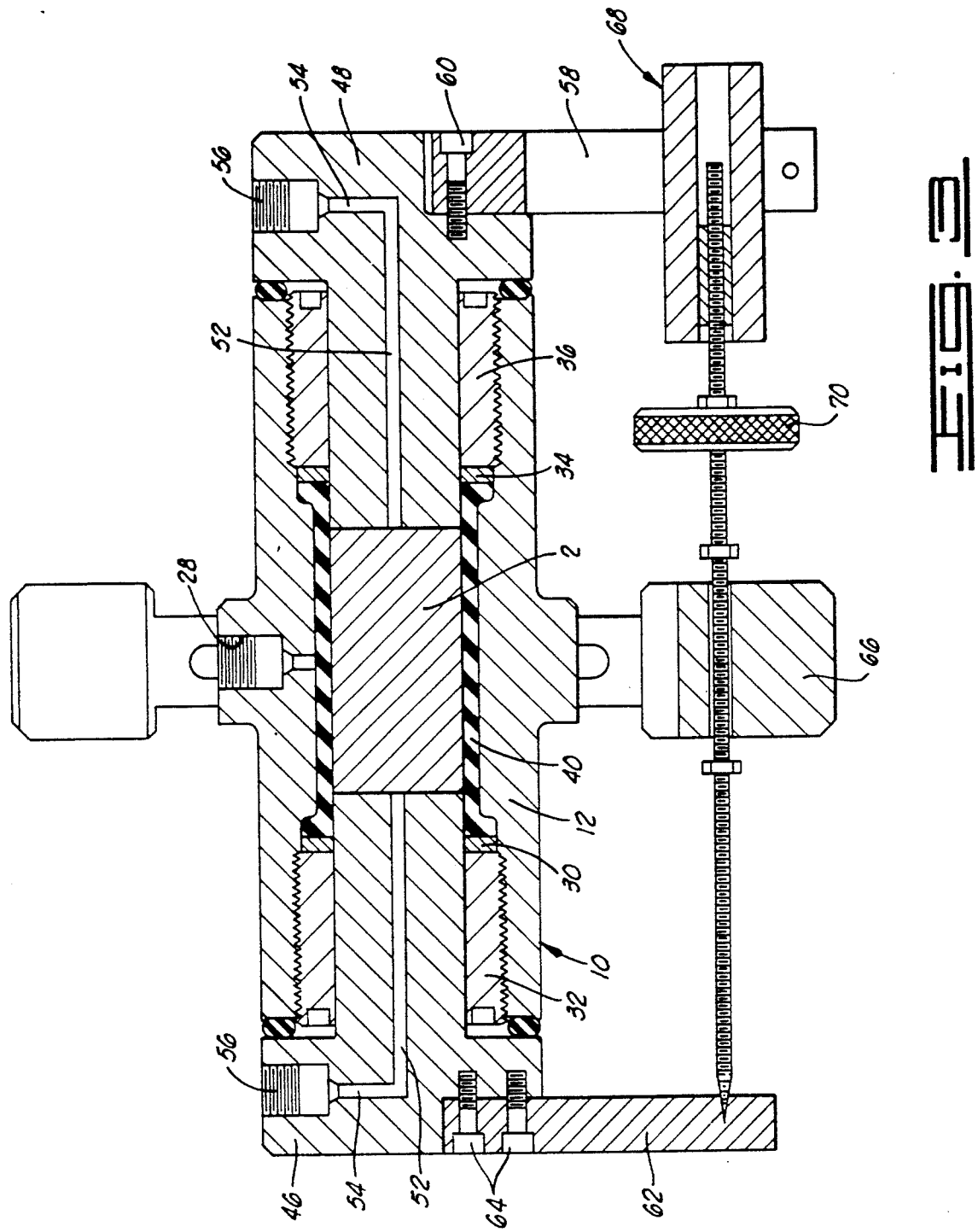

CORE SAMPLE TEST METHOD AND APPARATUS

BACKGROUND OF THE INVENTION

This invention relates generally to methods and apparatus for testing core samples extracted from an oil or gas well. In particular, the invention relates to a method of determining elastic properties of a core sample and an apparatus useful in performing the method, which apparatus is for detecting changes in longitudinal and lateral dimensions of the core sample.

A commonly utilized technique for stimulating the production of hydrocarbons from a subterranean rock formation penetrated by a well bore is to create and extend fractures in the formation. Generally, the fractures are created by applying hydraulic pressure on the formation from the well bore. That is, a fracturing fluid is pumped through the well bore and into the formation at a rate and pressure such that the resultant hydraulic force exerted on the formation causes one or more fractures to be created. The fractures are extended by continued pumping; and the fractures can be propped open or flow channels can be etched in the faces of the fractures with acid, or both can be done, to provide openings in the formation through which hydrocarbons readily flow to the well bore. Fracturing is also utilized in carrying out enhanced production procedures in subterranean formations (e.g., water flooding from an injection well to a production well) as well as in other applications.

In designing fracturing treatments to be carried out in subterranean rock formations, it is often necessary and always desirable to know the direction in which fractures will extend in the formation. Such knowledge enables more efficient reservoir management. For example, knowing such directional information allows one to better place production wells for maximizing production from the reservoir of hydrocarbons in the subterranean formation and to better place waterflood injection wells for increasing waterflood sweep efficiency by avoiding an injection well arrangement that would cause premature breakthrough of the injected fluid into the producing well.

Information that can be used to help predict fracture direction includes Young's modulus and Poisson's ratio, which describe elastic properties of rock. These can be determined by testing rock core samples that have been extracted from an oil or gas well in a known manner.

Young's modulus can be defined as the ratio of normal stress to the resulting strain in the direction of the applied stress. Stress can be applied to a core sample with a longitudinal or axial compressive force from a known type of press. The resulting longitudinal or axial strain is the yield or deflection measurable as the change in the longitudinal or axial dimension of the core sample.

Poisson's ratio can be defined as the ratio of lateral or radial strain to the longitudinal or axial strain for normal stress within the elastic limit. This is measurable using the aforementioned detected dimensional change in conjunction with a lateral or radial dimensional change detected in response to the applied stress.

There are prior types of core sample test methods and apparatus with which to apply forces to core samples and measure responses to such forces; however, we are not aware of any in which core samples can be tested and removed without removing a sealing sleeve from inside a supporting housing of a test instrument and in which both longitudinal yield and lateral yield can be concurrently sensed and in which such sensing can be done under temperatures up to about 300° F. and radial and pore pressures up to about 10,000 psi to better simulate actual downhole conditions and thereby provide more accurate indications of formation properties. To facilitate testing and to provide more useful information, there is the need for an improved method and apparatus for testing core samples which has the aforementioned features we do not find in any one prior test method or apparatus of which we are aware.

SUMMARY OF THE INVENTION

The present invention overcomes the above-noted and other shortcomings of the prior art and meets the aforementioned need by providing a novel and improved method and apparatus for testing a core sample from an oil or gas well. With the present invention, core samples can be tested and replaced without removing a sealing sleeve from inside a supporting housing of a test instrument, both longitudinal yield and lateral yield can be concurrently sensed, and such sensing can be done under temperatures up to about 300° F. and radial and pore pressures up to about 10,000 psi.

The present invention provides a method of determining elastic properties of a core sample taken from an oil or gas well, comprising: (a) moving the core sample into a sealing member of a test vessel further including a housing supporting the sealing member; (b) applying a force to the core sample in the sealing member; (c) sensing a change in longitudinal dimension of the core sample; and (d) sensing a change in lateral dimension of the core sample. Steps (c) and (d) are preferably performed concurrently, and these steps provide information with which to determine Young's modulus and Poisson's ratio. It is also a preferred aspect of the present invention that the core sample be inserted into and removed from the sealing member without removing the sealing member from the housing.

The present invention also provides an apparatus for detecting changes in longitudinal and lateral dimensions of a core sample extracted from an oil or gas well, comprising: a housing; a sealing sleeve fixed inside the housing and adapted to receive a core sample without the sealing sleeve being removed from the housing; retaining means for releasably retaining the core sample within the sealing sleeve and for transferring a longitudinal force to the core sample; longitudinal deflection sensing means for sensing a change in longitudinal dimension of the core sample in response to an applied longitudinal force; and lateral deflection sensing means for sensing a change in lateral dimension of the core sample in response to the applied longitudinal force.

Therefore, from the foregoing, it is a general object of the present invention to provide a novel and improved method and apparatus for testing a core sample from an oil or gas well. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 1 is an end view of a preferred embodiment apparatus of the present invention.

FIG. 2 is a sectional view of the apparatus taken along line 2—2 in FIG. 1.

FIG. 3 is a sectional view of the apparatus taken along line 3—3 in FIG. 1.

FIG. 4 is an enlarged view of a portion of FIG. 2 more clearly showing the interface between a lateral sensor and a core sample.

DETAILED DESCRIPTION OF PREFERRED EMBODIMENT

Referring principally to FIG. 2, the preferred embodiment of an apparatus for detecting changes in longitudinal and lateral dimensions of a core sample 2 extracted from an oil or gas well will be described. This apparatus can be used, preferably in the upright orientation of FIG. 2 or inverted therefrom, in performing the method of the present invention.

The core sample 2 is typically cylindrical with two ends 4, 6 and a side 8 extending between the ends 4, 6. It is extracted from an oil or gas well in a manner known in the art.

The apparatus of the present invention comprises a housing 10 defining a chamber in which the core sample 2 is tested. The housing 10 includes a unitary support body 12 having a contoured cylindrical inner surface 14 providing support shoulders 16, 18. An axially central, radially innermost surface portion 14a is defined at a smaller diameter than radially outermost threaded surface portions 14b, 14c extending longitudinally from opposite ends of the central surface portion 14a. A circumferential flange 20 protrudes radially outwardly from a central portion of a cylindrical outer surface 22 of the support body 12. Two diametrically opposed openings 24, 26 are defined radially through the flange 20, and an opening 28 (FIG. 3) angularly offset from the openings 24, 26 is also defined through the flange 20.

Forming removable parts of the housing 10 are an annular washer 30, an exteriorly threaded annular holding member 32 connected to the threaded surface 14b of the support body 12 and adjacent the washer 30 to hold it in place, an annular washer 34, and an exteriorly threaded annular holding member 36 connected to the threaded surface 14c of the support body 12 and adjacent the washer 34 to hold it in place. The holding members 32, 36 have sockets 38 defined in their outer ends for receiving a spanner wrench to screw and unscrew the members 32, 36 relative to the support body 12; however, other constructions and configurations for inserting and removing the holding members can be used (e.g., engagement heads protruding from the main body, a T-shaped body, etc.). Furthermore, the washers 30, 34 can be of various designs. For example, although shown as flat in FIGS. 2 and 3, each washer 30, 34 can have a curved side that engages the respective end of a sealing sleeve 40 to increase sealing pressure thereagainst when secured by the respective holding member 32, 36. The washers 30, 34 can also carry sealing members, such as a respective O-ring on the washer's inner circumference.

The apparatus of the present invention further comprises the aforementioned sealing sleeve 40, which is supported inside the housing 10 and adapted to receive the core sample 2 without the sealing sleeve 40 being removed from the housing 10. The sleeve is made of a resilient material of a type known in the art, and is preferably what is referred to as a Hassler sleeve.

The illustrated sealing sleeve 40 has a cylindrical main body portion 40a with radially outwardly flaring ends 40b, 40c (however, to facilitate sliding the sleeve 40 into or out of the support body 12 upon assembling or re-assembling the apparatus, one end such as end 40c can have a straight configuration). These illustrated ends 40b, 40c are adjacent the shoulders 16, 18, respectively, of the support body 12, and the main body portion 40a of the sealing member is adjacent the surface 14a of the support body 12. This relationship properly locates the sleeve 40 relative to the support body 12 during assembly. This positioning also remains fixed by means of the washer/holding member pairs 30, 32 and 34, 36 disposed adjacent respective ends of the sealing sleeve 40. Two diametrically opposed openings 42, 44 are defined in the sleeve 40 and aligned with the openings 24, 26, respectively, of the support body 12.

The apparatus also comprises retaining means for releasably retaining the core sample 2 within the sealing sleeve 40 and for transferring a longitudinal force to the core sample 2. The retaining means of the preferred embodiment includes two end caps 46, 48 slidably received in the housing 10 (specifically, within the washer/holding member pairs 30, 32 and 34, 36, respectively). Each end cap 46, 48 has an axial channel 52 and an intersecting radial channel 54 (FIG. 3). Each channel 52 opens through the end of the respective end cap that is adjacent a respective end of the core sample 2 when the apparatus is assembled as illustrated. Each channel 54 opens through the side of its respective end cap via a respective port 56 (FIG. 3). Each of the end caps 46, 48 has a smaller diameter cylindrical portion that is received into the housing and a larger diameter cylindrical portion that is outside the housing as shown in the drawings. The sides of the smaller diameter portions are preferably smooth so that the end caps can be easily pushed in and pulled from the housing 10 when there is no test pressure being applied.

Referring primarily to FIG. 3, connected to the end caps 46, 48 is a longitudinal (specifically, axial in the preferred embodiment) deflection sensing means for sensing a change in longitudinal dimension of the core sample 2 in response to an applied force. A support bracket 58 is connected by a screw 60 to the end cap 48, and a support bracket 62 is connected by screws 64 to the end cap 46. Supported by the brackets 58, 62 and by a central split annular support collar 66 is a direct current linearly variable differential transducer assembly 68 including a calibration nut 70. The assembly 68 is of conventional type, such as a Schaevitz model 050-DC-E (with core).

Referring to FIG. 1, the support collar 66 is connected to the housing 10 by screws 72 that pass through the collar 66 and tighten against the flange 20 of the support body 12.

Referring primarily to FIG. 2, also supported by the collar 66 is lateral (specifically, radial in the preferred embodiment) deflection sensing means for sensing a change in lateral dimension of the core sample 2 in response to the applied force. In the preferred embodiment this includes two sensors 74, 76 having respective probes communicating through the sealing sleeve 40 to detect lateral change in the core sample 2. Each of the sensors 74, 76 includes a direct current linearly variable differential transducer assembly which can be of the same type as used for the longitudinal sensor. More clearly shown in FIG. 4, the transducer of the sensor 74 has a probe 78 that is received (such as by being pushed or threaded) in an insert 80 in the opening 42 defined through the sealing sleeve 40. A seal 82 and a retainer nut 84 seal and secure the sensor 74 relative to the support collar 66. The sensor 76 is likewise disposed relative to the opposing opening 44 in the sealing sleeve 40 as is apparent from FIG. 2.

One way to combine the inserts 80 and the sealing sleeve 40 includes inserting new brass inserts 80 into a forming fixture and pressing a mandrel of suitable size and shape against each such insert to give its head a suitable curvature to conform it to the shape of core samples to be tested. The sealing sleeve 40, having been put in the support body 12 and having had the openings 42, 44 defined therein (such as by punching with an awl), is removed from the support body 12 and the shaped inserts 80 are inserted through their respective openings 42, 44 and sealed with a suitable sealant (e.g., Permatex gasket sealant).

It is contemplated that other sensing and mounting devices and constructions can be used.

Mounted adjacent outer surface 22 of the support body 12 are heater bands 86 (FIG. 2, not shown in FIG. 3). These are conventional devices, such as mineral insulated heater bands from Omega Engineering, Inc. (e.g., 2.125-inch inner diameter, 120 volts, 400 watts, Chromalox).

The metallic components of the preferred embodiment housing and end caps depicted in the drawings are of any suitable material, such as stainless steel. The sealing elements are of any suitable material, such as an elastomer, that can be machined or preferably molded. All should be adapted for use in the high temperature, high pressure test environment preferably used.

The present invention also provides a method of determining elastic properties of a core sample taken from an oil or gas well. This will be described with reference to the preferred embodiment apparatus shown in the drawings.

The method comprises moving (preferably either pushing or dropping) the core sample 2 into the axial opening defined in the sealing member 40 of the test vessel that includes the housing 10 which supports the sealing member 40. The test vessel is closed by pushing the end members 46, 48 into the axial channel defined through the housing 10, wherein the stem of each end cap is adjacent the respective retaining member, washer and end of the sealing sleeve 40 as illustrated. The end members 46, 48 are movable relative to the housing 10 and the sealing member 40. The end caps are preferably slidable for easy insertion and extraction and for permitting movement in response to a longitudinal force applied by a press. When the end caps are installed as shown in the drawings, they support the core sample 2 at its two ends 4, 6. In the illustrated embodiment, installed in conjunction with the end caps 46, 48 are respective spacers 88. The spacers 88 allow the core sample 2 to center or adjust itself in response to confining pressure being applied (i.e., the core sample 2 can move from both ends). The spacers 88 can be any suitable device, such as a flexible O-ring or a split ring member.

To test the core sample 2 thus loaded in the housing 10 and sealing sleeve 40, pressure is applied and resultant dimensional changes are sensed by the sensors 68, 74, 76. A compressive axial force can be applied to the core sample 2. This can be done by applying a force from a conventional press to the end members 46, 48 so that the end members 46, 48 move relatively closer to each other and thereby exert a force on the core sample 2 held therebetween in the sealing member 40. Furthermore, confining pressure can be applied radially toward the sealing member 40 by pumping a fluid through the opening 28 into the housing 10 around the outside of the sealing member 40. This simulates a well pressure and preferably can be up to at least about 10,000 psi. In the preferred embodiment, a minimal (e.g., 50–100 psi) confining pressure is first applied through opening 28; the spacers 88 may then be removed (but they do not necessarily have to be if they are sufficiently deformable); then full pressure load (either or both axial and confining) can be applied.

Due to the symmetrical construction of the apparatus shown in the drawings, confining pressure is free to go from both ends of the core sample 2 to the center. Thus, the core sample 2 is free to give from both ends in response to the applied force(s). This keeps the greatest lateral or radial dimensional changes at the center of the core sample 2 where the transducers 74, 76 are located, thereby ensuring reliable and consistent measurements from one core sample to another.

Pore pressure can also be applied to the core sample 2. This is done by pumping a fluid under pressure (up to but not exceeding the confining pressure) against at least one of the ends of the core sample 2. This pressure is applied through either or both of the ports 56 in the end members 46, 48.

The core sample 2 can be heated by electrically energizing the heating jackets 86. Heating preferably occurs until the temperature inside the sealing member 40 is at a temperature simulating a well temperature, such as up to 300° F.

With the desired conditions of the core sample 2 set, the resulting dimensional changes are sensed. This includes sensing the longitudinal or axial distance the core sample 2 is compressed as indicated by an electrical signal provided by the linearly variable differential transducer 68 in response to the movement between the two end members 46, 48 holding the core sample 2 in the sealing member 40. Calibration such as for deformation of the end caps 46, 48 can be made via the calibration nut 70. A measurement of the distance or length of deformation can be determined from the transducer signal as known in the art.

Sensing dimensional changes also includes sensing the radial distance the core sample 2 is distended in response to the forces acting on the core sample. The radial deformation is sensed by measuring at two locations around the core sample, namely those locations where the linearly variable differential transducers 74, 76 are disposed in the inserts 80 that contact the core sample 2. Electrical signals from the transducers 74, 76 are used in known manner to provide measurements of the dimensional change. Calibration is made by respective calibration screws.

In the preferred embodiment, the aforementioned steps of sensing dimensional changes are performed concurrently. This is possible by using both the longitudinal and the lateral transducers in a single test apparatus as described.

Because the dimensional changes represent axial and radial strain of the cylindrical core sample 2 under the stress(es) applied by the exerted force(s), the preferred embodiment method of the present invention further comprises determining Young's modulus and Poisson's ratio. This is done in known manner in response to the applied stress and resultant measured strain.

Once the core sample 2 has been tested and the pressure and temperature returned to ambient conditions, the core sample 2 can be easily removed so that another core sample can be tested by repeating the foregoing steps if desired. The core sample 2 is removed from the sealing member 40 without removing the sealing member 40 from the housing 10. This is done by removing one or both of the end members 46, 48 from the test vessel and quickly and easily sliding the core sample 2 out without removing the sealing member 40. Another core sample can then be quickly loaded in by sliding or dropping it into the retained sealing sleeve 40. Therefore, the present invention is reusable without requiring replacement or manipulation of the sealing sleeve 40 (unless, for example, it has been damaged).

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

What is claimed is:

1. An apparatus for detecting changes in longitudinal and lateral dimensions of a core sample extracted from an oil or gas well, comprising:
   a housing;
   a sealing sleeve fixed inside said housing and adapted to receive a core sample without said sealing sleeve being removed from said housing;
   retaining means for releasably retaining the core sample within said sealing sleeve and for transferring a longitudinal force to the core sample;
   longitudinal deflection sensing means for sensing a change in longitudinal dimension of the core sample in response to an applied longitudinal force;
   lateral deflection sensing means for sensing a change in lateral dimension of the core sample in response to the applied longitudinal force; and wherein:
   said housing includes:
   a support body having a contoured inner surface providing a support shoulder for fixedly supporting said sealing sleeve inside said body;
   a first washer disposed adjacent and end of said sealing sleeve;
   a first annular holding member connected to said body adjacent said first washer;
   a second washer disposed adjacent another end of said sealing sleeve; and
   a second annular holding member connected to said body adjacent said second washer; and
   said retaining means includes:
   a first end cap slidably received in said first annular holding member; and
   a second end cap slidably received in said second annular holding member.

2. An apparatus as defined in claim 1, wherein said longitudinal deflection sensing means is connected to said first and second end caps, and said lateral deflection sensing means includes two sensors communicating through said sealing sleeve.

3. An apparatus as defined in claim 2, wherein:
   said longitudinal deflection sensing means includes a first linearly variable differential transducer; and
   said two sensors of said lateral deflection sensing means include second and third linearly variable differential transducers.

4. An apparatus as defined in claim 3, further comprising a support collar connected to said housing and supporting said first, second and third linearly variable differential transducers.

5. An apparatus as defined in claim 1, wherein:
   said longitudinal deflection sensing means includes a first linearly variable differential transducer; and
   said lateral deflection sensing means includes second and third linearly variable differential transducers.

6. An apparatus as defined in claim 5, further comprising a support collar connected to said housing and supporting said first, second and third linearly variable differential transducers.

* * * * *